United States Patent
Hinman et al.

(10) Patent No.: US 8,728,118 B2
(45) Date of Patent: May 20, 2014

(54) TOOL WITH END EFFECTOR FORCE LIMITER

(71) Applicant: Intuitive Surgical Operations, Inc., Sunnyvale, CA (US)

(72) Inventors: Cameron D. Hinman, Thurmond, NC (US); Karrie S. Bertsch, San Jose, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

(21) Appl. No.: 13/787,471

(22) Filed: Mar. 6, 2013

(65) Prior Publication Data

US 2013/0218140 A1   Aug. 22, 2013

Related U.S. Application Data

(63) Continuation of application No. 11/787,599, filed on Apr. 16, 2007, now Pat. No. 8,409,244.

(51) Int. Cl.
*A61B 17/00* (2006.01)

(52) U.S. Cl.
USPC .............................. 606/205; 606/51; 606/52

(58) Field of Classification Search
USPC ..................... 606/205–209, 51, 52
See application file for complete search history.

(56) References Cited

U.S. PATENT DOCUMENTS

| | | | | |
|---|---|---|---|---|
| 5,403,342 A | * | 4/1995 | Tovey et al. | 606/205 |
| 5,562,699 A | * | 10/1996 | Heimberger et al. | 606/205 |
| 5,643,248 A | * | 7/1997 | Yoon | 606/1 |
| 5,683,412 A | * | 11/1997 | Scarfone | 606/205 |
| 5,782,834 A | * | 7/1998 | Lucey et al. | 606/22 |
| 6,068,624 A | * | 5/2000 | Benecke et al. | 606/1 |
| 2005/0277956 A1 | * | 12/2005 | Francese et al. | 606/142 |

* cited by examiner

*Primary Examiner* — Darwin Erezo
*Assistant Examiner* — Katrina Stransky

(57) ABSTRACT

The invention provides surgical or diagnostic tools and associated methods that offer improved user control for operating remotely within regions of the body. In some embodiments these tools include a proximally-located actuator for the operation of a distal end effector, as well as proximally-located actuators for articulational and rotational movements of the end effector. Control mechanisms and methods refine operator control of end effector actuation and of these articulational and rotational movements. A force limiter mechanism protects the end effector and manipulated objects from the harm of potentially excessive force applied by the operator. The tool may also include other features. A multi-state ratchet for end effector actuation provides enablement-disablement options with tactile feedback. An articulation lock allows the fixing and releasing of both neutral and articulated configurations of the tool and of consequent placement of the end effector. A rotation lock provides for enablement and disablement of rotatability of the end effector.

25 Claims, 17 Drawing Sheets

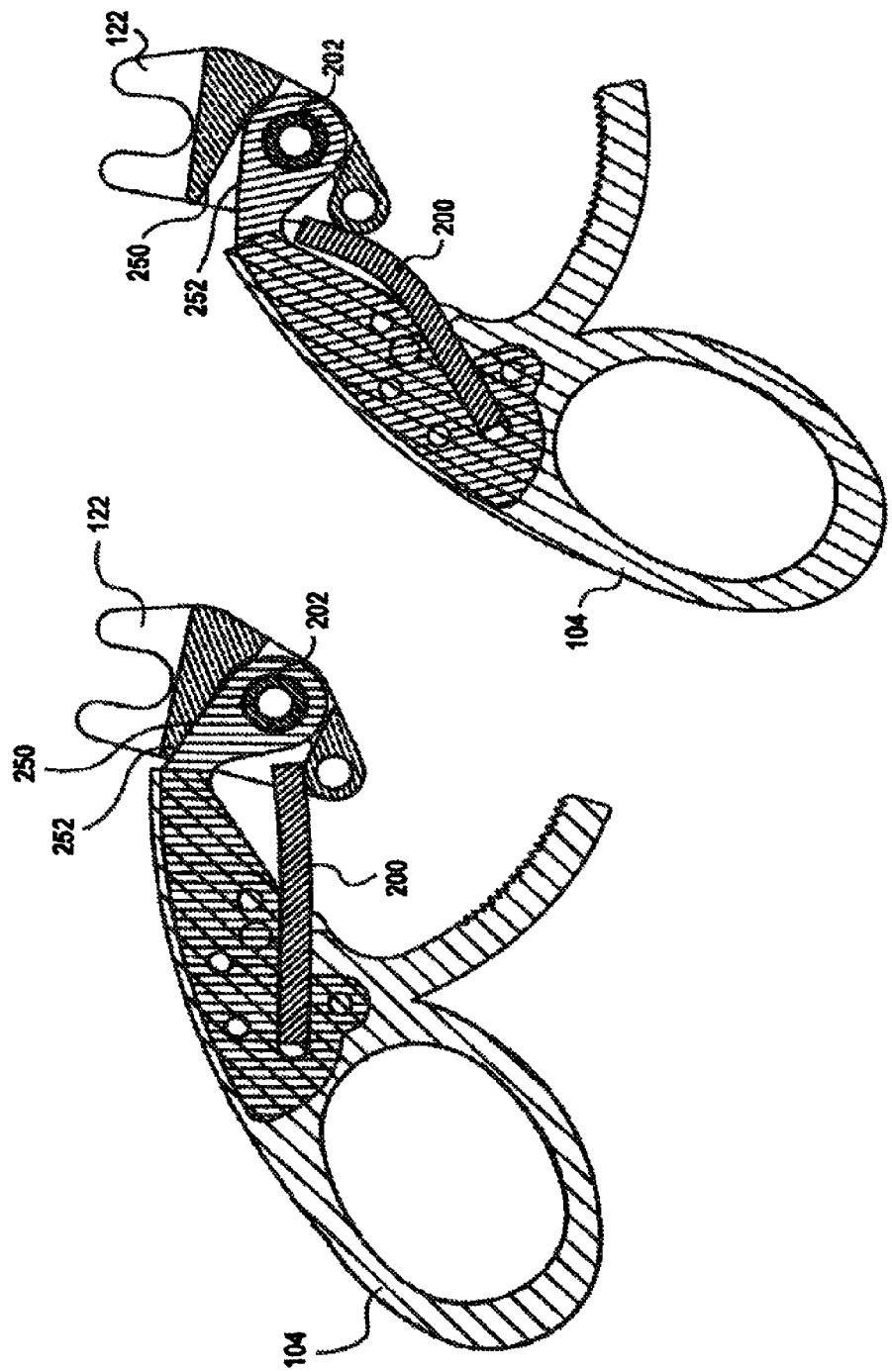

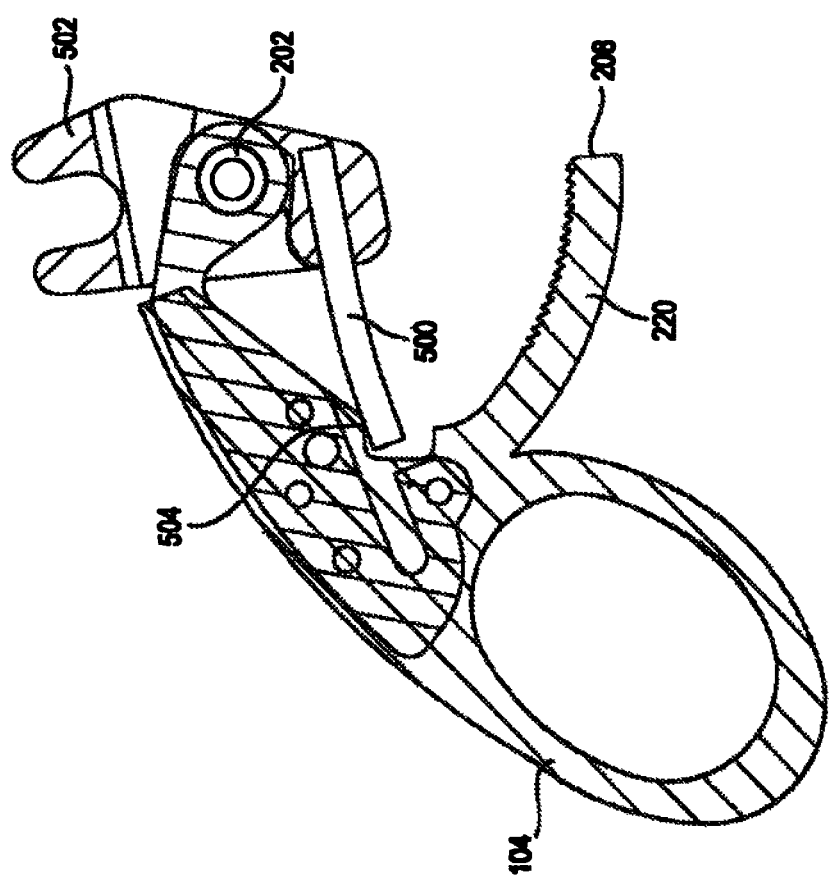

TOOL WITH END EFFECTOR FORCE LIMITER

CROSS REFERENCE TO RELATED APPLICATIONS

This application is a continuation patent application of U.S. patent application Ser. No. 11/787,599, filed Apr. 16, 2007, now U.S. Pat. No. 8,409,244 and entitled "Tool With End Effector Force Limiter," which is incorporated by reference herein, in its entirety. This application is related to the following concurrently filed U.S. patent applications: Ser. No. 11/787,543 entitled "Tool with articulation lock" of Hegeman, Danitz, and Alvord, Ser. No. 11/787,605 entitled "Tool with multi-state ratcheted end effector" of Hinman, Ser. No. 11/787,607 entitled "Tool with rotation lock" of Hinman and Danitz, and Ser. No. 11/787,608 entitled "Articulating tool with improved tension member system" of Hegeman, Danitz, Bertsch, and Alvord.

INCORPORATION BY REFERENCE

All publications and patent applications mentioned in this specification are herein incorporated by reference to the same extent as if each individual publication or patent application was specifically and individually indicated to be incorporated by reference.

FIELD OF THE INVENTION

This invention relates to tools with end effectors whose actuators control aspects of end effector operation.

BACKGROUND OF THE INVENTION

The popularity of minimally invasive surgery has been growing rapidly due to its association with decreased complication rates and post-surgical recovery times. The instruments employed are generally hand-operable and typically include a handle, a shaft that may or may not be rotatably attached to the handle, a rotation knob rigidly fixed to the proximal end of the shaft near the handle in instances where the shaft is rotatably attached to the handle, and a tool or end effector attached to the distal end of the shaft. To manipulate the instruments, they are held at the handle and typically pivoted about a pivot point defined by the entry incision, i.e., the incision made in the abdominal wall for laparoscopic procedures. The end effector may also be rotated about the shaft axis, as for example, by rotating a rotation knob, if present. In use, these instruments have limited control and range of motion and become physically taxing as the length of the procedure increases.

Surgical procedures such as endoscopy and laparoscopy typically employ instruments that are steered within or towards a target organ or tissue from a position outside the body. Examples of endoscopic procedures include sigmoidoscopy, colonoscopy, esophagogastroduodenoscopy, and bronchoscopy, as well as newer procedures in natural orifice transluminal endoscopic surgery ("NOTES"). Traditionally, the insertion tube of an endoscope is advanced by pushing it forward, and retracted by pulling it back. The tip of the tube may be directed by twisting and general up/down and left/right movements. Oftentimes, this limited range of motion makes it difficult to negotiate acute angles (e.g., in the rectosigmoid colon), creating patient discomfort and increasing the risk of trauma to surrounding tissues.

Laparoscopy involves the placement of trocar ports according to anatomical landmarks. The number of ports usually varies with the intended procedure and number of instruments required to obtain satisfactory tissue mobilization and exposure of the operative field. Although there are many benefits of laparoscopic surgery, e.g., less postoperative pain, early mobilization, and decreased adhesion formation, it is often difficult to achieve optimal retraction of organs and maneuverability of conventional instruments through laparoscopic ports. In some cases, these deficiencies may lead to increased operative time or imprecise placement of components such as staples and sutures.

Recently, surgical instruments, including minimally invasive surgical instruments, have been developed that are more ergonomic and which have a wider range of motion and more precise control of movement. These instruments may include mechanisms that articulate using a series of links coupled with one or more sets of tension bearing members, such as cable. As with conventional instruments used in minimally invasive surgery, rotation of the shaft and end effector with respect to the handle is an important feature of cable and link type instruments to aid with dissecting, suturing, retracting, knot tying, etc. Ergonomic, flexible, and intuitive mechanisms that facilitate manual control of the end effectors of such instruments are also important factors as medical procedures become more advanced, and as surgeons become more sophisticated in their operating abilities. Further improvements in the features and design of surgical instruments are desirable.

SUMMARY OF THE INVENTION

Some surgical or diagnostic instruments have an end effector whose operation is controlled by a movable end effector actuator. In particular, some instruments have operation states in which a force applied to the end effector actuator may be reflected in a force delivered by the end effector. It may at times be desirable to limit the force delivered by the end effector, regardless of the amount of force applied to the end effector actuator. This invention provides methods and devices for limiting the force delivered by an end effector.

Some embodiments of the invention comprise a surgical or diagnostic tool comprising an end effector at a distal end of the tool and an end effector actuator at a proximal end of the tool. The end effector actuator is operatively connected to the end effector through a linkage to deliver an actuation force from the end effector actuator to the end effector in response to movement of the end effector actuator. The tool further comprises a force limiter adapted to establish an upper limit on the actuation force that may be delivered to the end effector by the end effector actuator.

In some embodiments, the tool further comprises a handle supporting the end effector actuator, the end effector actuator being movable with respect to the handle. The tool may comprise a stop element engagable with the end effector actuator to stop its motion. In some embodiments, the force limiter is adapted to deform in response to actuation force delivered by the end effector actuator.

Some embodiments of the force limiter comprise a spring in the linkage. The spring may be pre-loaded to a pre-determined stress within the linkage. The spring may be formed from a superelastic shape memory material treated so as to bend when the upper limit of the actuation force is applied to the end effector by the end effector actuator. The superelastic shape memory material may have a plateau stress level, and the spring may be disposed within the linkage so at to be pre-loaded at least about to the plateau stress level. The tool may include both a spring and a stop element engagable with the end effector actuator to stop its motion.

In some embodiments, the end effector is operably connected to the end effector actuator at least in part through the force limiter. The force limiter may be disposed between the end effector actuator and the linkage. In some embodiments, the end effector actuator is operably connected to the linkage such that movement of the end effector actuator moves the linkage. Movement of the end effector actuator with respect to the linkage may vary when the upper limit of the actuation force is reached.

In some embodiments the force limiter comprises a tension bearing member in the linkage. In some of these embodiments, the tension member includes a superelastic shape memory material that may be pre-stretched to a predetermined stress when assembled into the linkage. In some typical embodiments, the predetermined stress may correspond approximately to the upper limit of the actuation force that is to be applied to the end effector by the end effector actuator.

In some embodiments, the end effector comprises a movable force delivery surface, and in some embodiments, the end effector may comprise a pair of jaws. In some embodiments, the tool comprises a shaft disposed between the end effector and the end effector actuator. The tool may also comprise an articulation mechanism for manipulating angular orientation of the end effector with respect to the shaft. The articulation mechanism in turn may comprise a proximal link and a distal link spaced apart from the proximal link. In such embodiments, movement of the proximal link causes corresponding relative movement of the distal link and angular movement of the end effector with respect to the shaft.

Embodiments of the invention comprise a method of operating a surgical or diagnostic tool, the tool as summarized above, where the method of use comprises placing the end effector at a target site, applying an actuation force to the end effector actuator, delivering at least some of the actuation force through the end effector to the target site, and limiting the magnitude of the delivered actuation force to an upper limit.

The step of applying an actuation force may comprise moving the end effector actuator. In some embodiments, the tool used in the method further comprises a handle supporting the end effector actuator, and the step of moving the end effector actuator comprises moving the end effector actuator with respect to the handle. The tool may comprise a stop element, and the moving step may then comprise engaging the end effector actuator with the stop element.

The method of using a surgical or diagnostic tool, as summarized above, may include the use of a tool that further comprises a force limiter, and the limiting step of the method may further comprise deforming the force limiter. The force limiter may comprise a spring, and the limiting step may then comprise deforming the spring. In some embodiments, the deforming step comprises increasing strain of the spring without substantially increasing stress of the spring. In other embodiments, the force limiter comprises a tension bearing member, and the limiting step may include tensioning the member. In some of these embodiments, the deforming step may include the tension member stretching in response to the tensioning. In some of these embodiments, the step of limiting the magnitude of the delivered actuation force includes the stretching of the tension member.

The step of delivering the force may comprise moving the end effector, and the limiting step may comprise ceasing movement of the end effector despite continued movement of the end effector actuator. In some embodiments, the end effector comprises jaws, and the step of delivering a force to the target site comprising moving the end effector jaws.

In some embodiments of the method of use, the tool further comprises a handle supporting the end effector actuator and a shaft disposed between the handle and the end effector, and the method further comprises moving the handle angularly with respect to the shaft to move the end effector angularly with respect to the shaft.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings which are briefly described below.

FIG. 13 is a cross sectional view of the force limiter locale within the handle of a tool, showing the end effector actuator, force limiter, and rod actuator, the end effector actuator in an open position, the force limiter minimally bent at preload tension.

FIG. 14 is a cross sectional view of the force limiter locale within the handle as in FIG. 13, except the end effector actuator is in a closed position, the force limiter is fully bent, absorbing force from the closed end effector actuator.

FIG. 17 is a cross sectional view of the force limiter locale of an instrument showing the end effector actuator in an open position, and the force limiter having a minimal bend.

DETAILED DESCRIPTION OF THE INVENTION

Figure 1:
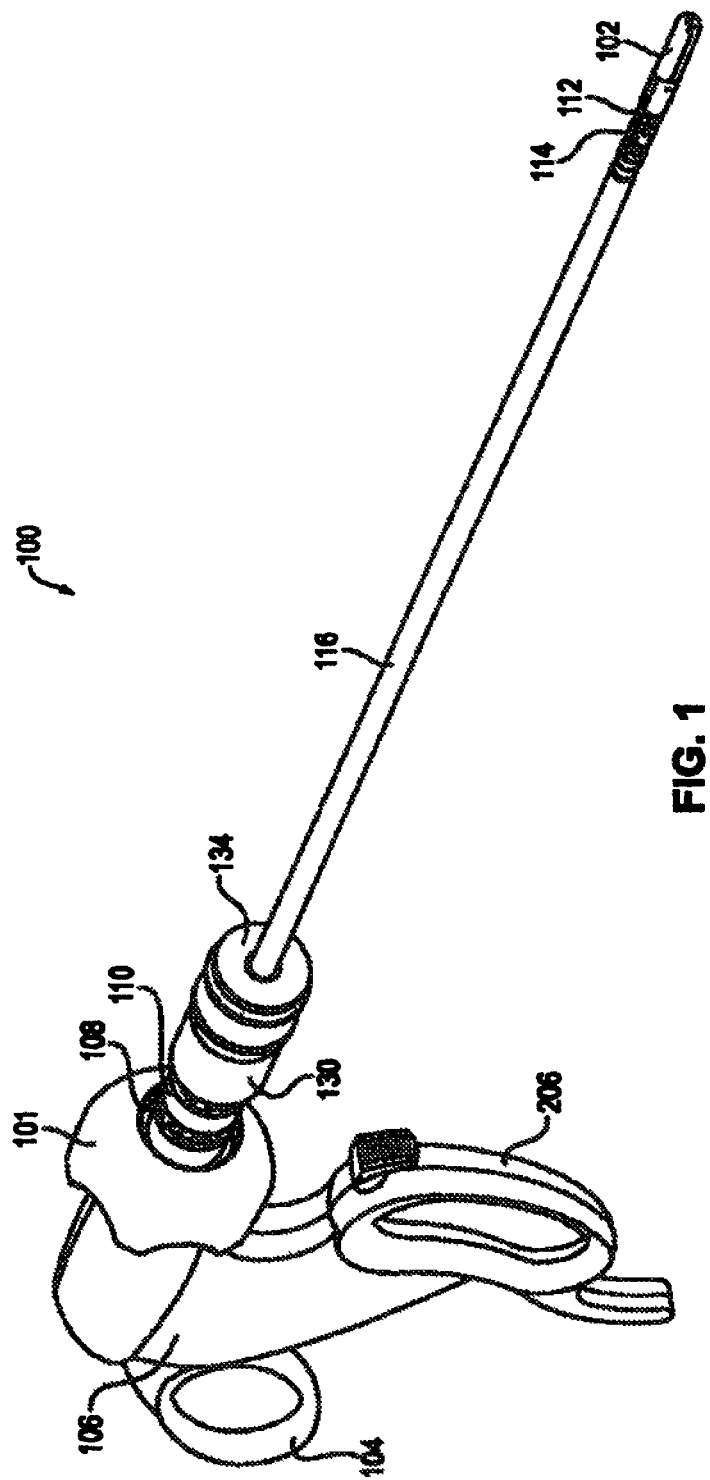
FIG. 1 is a front perspective view of an articulatable surgical tool.

The invention described herein relates to a force limiter mechanism intervening between force applied by a user at the proximal end of a tool and the transmission of that force to the distal end of a tool. Embodiments of the invention may be applied to non-articulating instruments, but many typical embodiments are applied to the operation of articulating tools. Steerable articulating instruments are described in U.S. Pat. No. 7,090,637; US 2005/0107667; US 2005/0273084; US 2005/0273085; and US 2006/0111210. The articulating mechanisms of the tools described in those publications use multiple pairs of segments or links controlled, e.g., by multiple sets of cables. Depending upon the specific design of the device, the links can be discrete segments (as described, e.g., in U.S. Pat. No. 7,090,637) or discrete portions of a flexible segment (as described, e.g., in US 2005/0173085). The instrument may also include steerable or controllable links of various types, e.g., as described in US 2005/0273084, US 2006/0111209, and US 2006/0111210. Some articulating or steerable instruments have an articulating capability provided by minimal numbers of link pairs and cables connecting such links, U.S. Pat. No. 5,916,146 of Alotta, for example, has a mechanism comprising a single pair of links controlled by a single cable.

When using such articulating instruments, a user may manipulate the proximal end of the instrument, thereby moving one or more proximal links of the articulation mechanism. This movement results in relative movement of the distal link(s) corresponding to the proximal link(s). It may at times be desirable to lock or otherwise maintain the straight or bent shape of the instrument. In certain embodiments of this invention, the shape of the instrument is maintained by preventing movement of at least one of the proximal links with respect to the rest of the instrument. In other embodiments, a friction-based articulation locking mechanism locks all links, proximal and distal; these embodiments are disclosed in the concurrently filed and hereby incorporated application "Tool with articulation lock" of Hegeman, Danitz, Hinman, and Alvord.

Many articulating instruments have end effectors controlled by movable actuators; a movable end effector actuator maybe, for example, a moveable portion of the handle of an instrument, or a thumbpiece. In some embodiments, the end effector actuator has an operation state in which movement is permitted in only one direction and an operation state in which the actuator is free to move in two or more directions. Certain embodiments of this invention provide methods and devices for changing the operational state of an end effector actuator between a state in which movement of the actuator is permitted in only one direction; a state in which the actuator is permitted to move in two directions in response to continuous user input to a state changer, and a state in which the actuator is permitted to in two directions in the absence of user input to a state changer.

FIGS. 1-20 show embodiments or portions of an articulatable tool 100 with an end effector 102 at its distal end and an end effector actuator 104 within a handle 106 at its proximal end. Instrument 100 may be used, e.g., in a laparoscopic procedure requiring grasping or cutting within a patient. Proximal articulation links 108 and 110 extend distally from handle 106, and distal articulation links 112 and 114 extend proximally from end effector 102. Proximal link 108 is connected to and moves with handle 106. Likewise, distal link 112 is connected to and moves with end effector 102. A bushing 115 separates links 110 and 112. Bushing 115 has convex surfaces at its proximal and distal ends that engage with corresponding concave surfaces on links 108 and 110. Further details of ball and socket links suitable for use with this invention may be found in US 2005/0273084, US 2006/0111209, and US 2006/0111210. An elongated shaft 116 is disposed between the proximal links and the distal links Embodiments of the shaft may either be rigid or flexible, although embodiments shown herein are depicted as being rigid.

Figure 3:
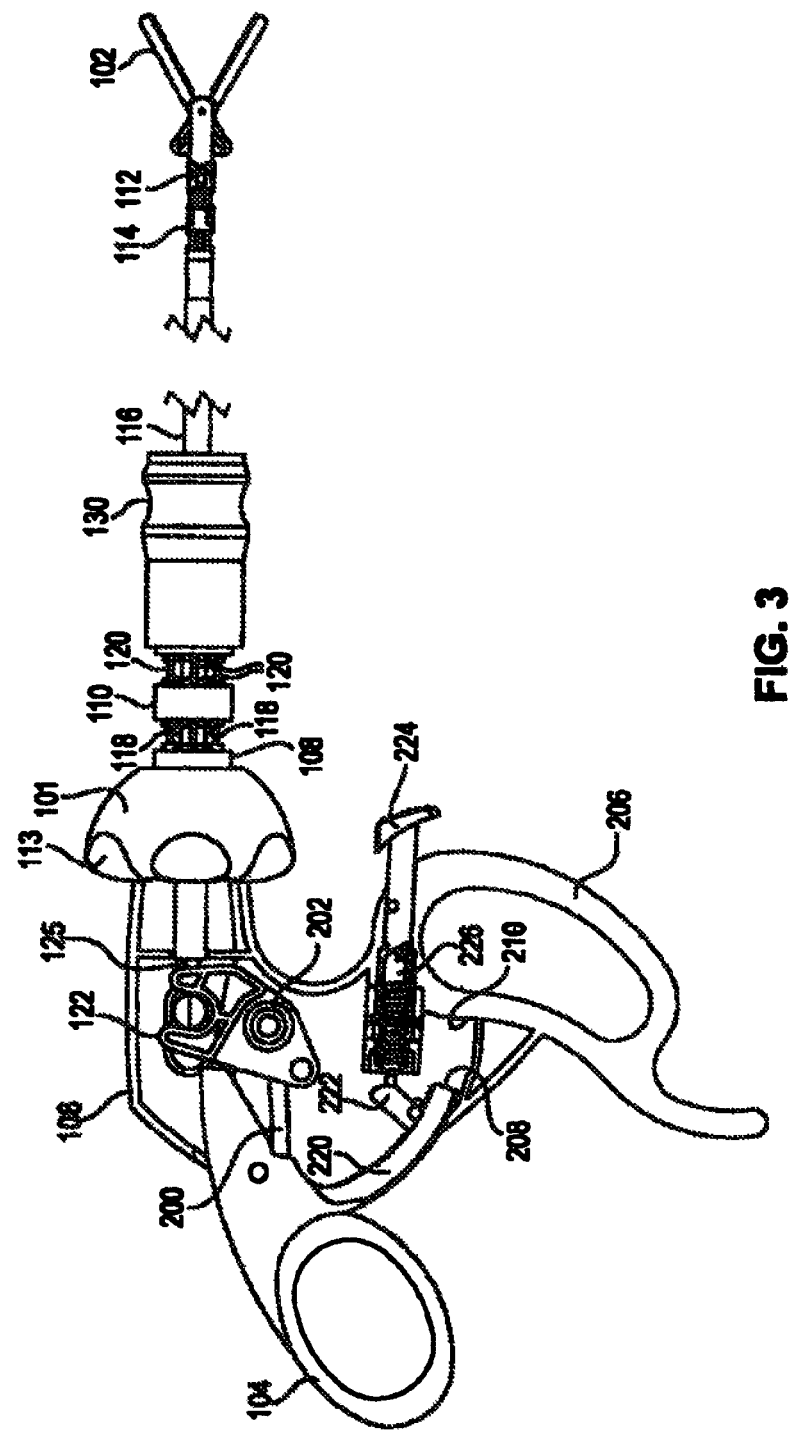
FIG. 3 is an exposed side view of a surgical tool with an end effector actuator and an end effector both in an open position.
Figure 4:
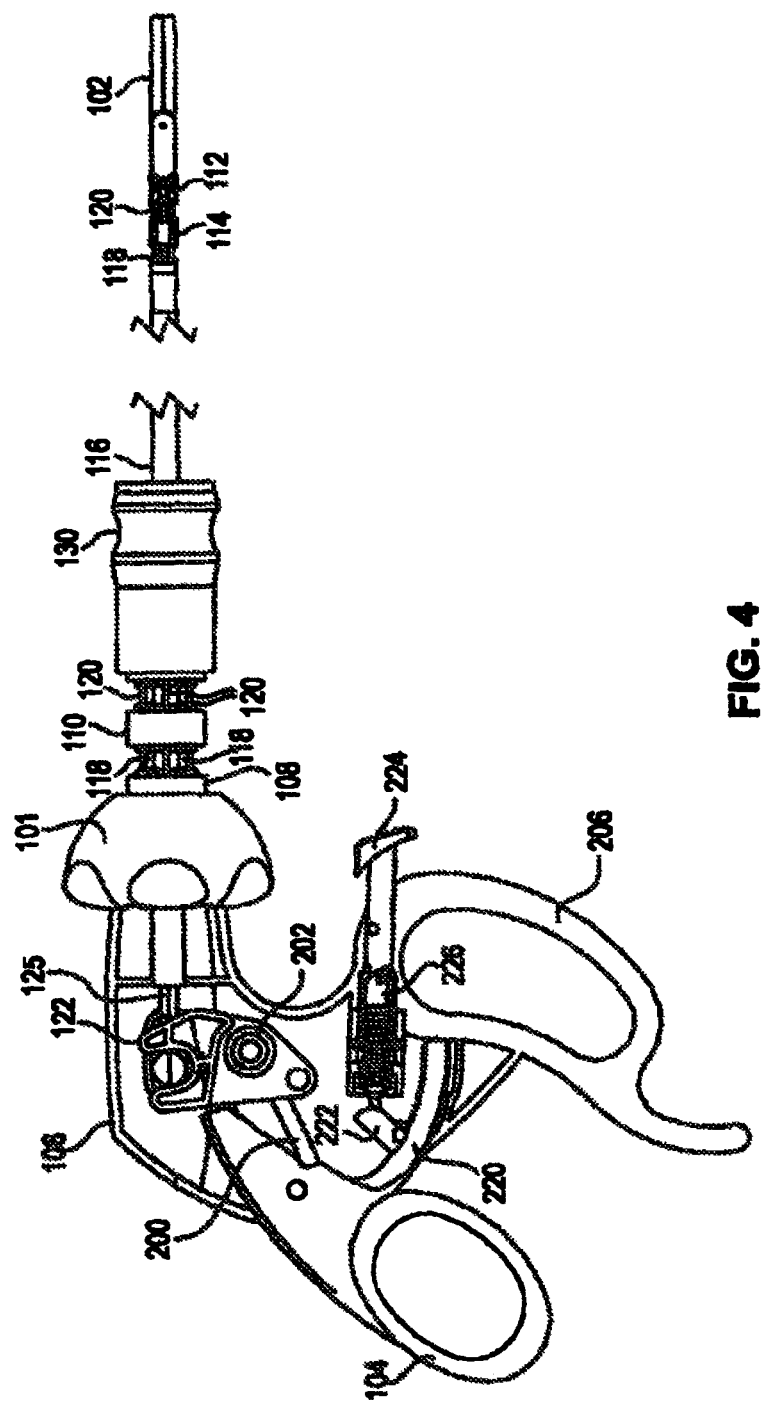
FIG. 4 is an exposed side view of a surgical tool with an end effector actuator and an end effector both in a closed position.
Figure 5:
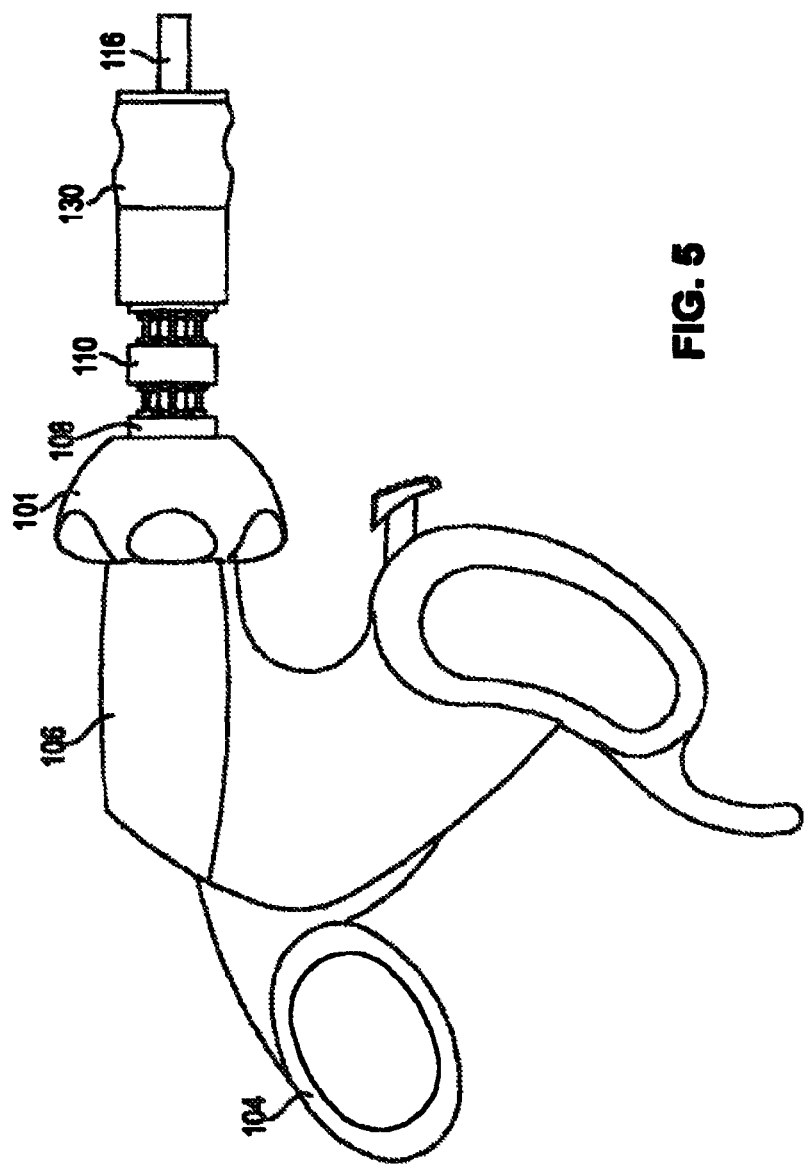
FIG. 5 is a side view of the proximal portion of a tool, showing the handle and proximal end of the shaft, with an articulation locking sleeve in a distal and unlocked position.

As seen in FIGS. 3 and 4, a set of control cables 118 is attached to proximal link 108, extends through proximal link 110, shaft 116 and distal link 114, and is attached to distal link 112. A second set of control cables 120 is attached to proximal link 110, extends through shaft 116 and is attached to distal link 114. In this embodiment, there are three control cables 118 in the first set and three control cables 120 in the second set. It should be appreciated, however, that other numbers of control cables may be used to connect corresponding proximal and distal links. In addition, mechanisms other than cables may be used to connect corresponding links.

Figure 2:
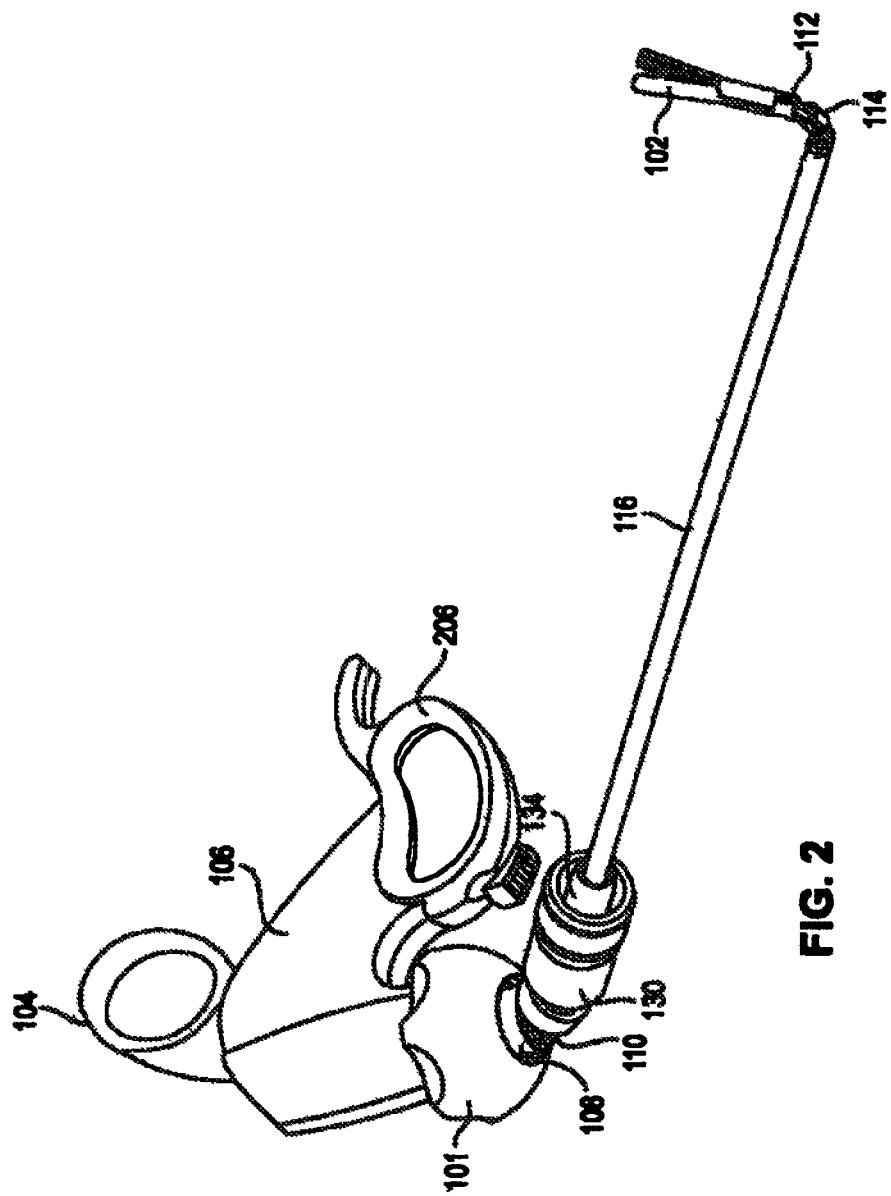
FIG. 2 is perspective view of a surgical tool in an articulated position.

As shown in FIG. 2, movement of handle 106 and proximal link 108 with respect to proximal link 110 moves end effector 102 and distal link 112 in a relative and corresponding manner. Likewise, movement of proximal link 110 with respect to shaft 116 moves distal link 114 with respect to shaft 116 in a relative and corresponding manner, also as shown in FIG. 2. This relative articulation movement provides a way for a user to remotely manipulate the end effector through movement of the handle. The relative movement of the distal link that corresponds to the proximal link movement may either mirror the movement of the proximal link or be reciprocal to it, depending on whether the cables are strung directly (for reciprocal movement), or whether they are rotated 180 degrees (for mirrored movement) between the proximal and distal links.

In order to maintain a particular position of the end effector with respect to the shaft, the articulating tool of this invention may have an articulation lock. In the embodiment shown in FIGS. 1-6, the articulation lock includes a movable rigid sleeve 130. In the unlocked position shown in FIGS. 1-5, sleeve 130 is distal to proximal links 108 and 110. In the locked position shown in FIG. 6, however, sleeve 130 has been moved proximally to a position adjacent to and covering links 108 and 110 as well as the proximal end of shaft 116, thereby blocking relative movement between links 108 and 110 and between link 110 and shaft 116. In this locked position, relative movement between distal links 112 and 114 and between link 114 and shaft 116 is prevented as well.

Figure 6:
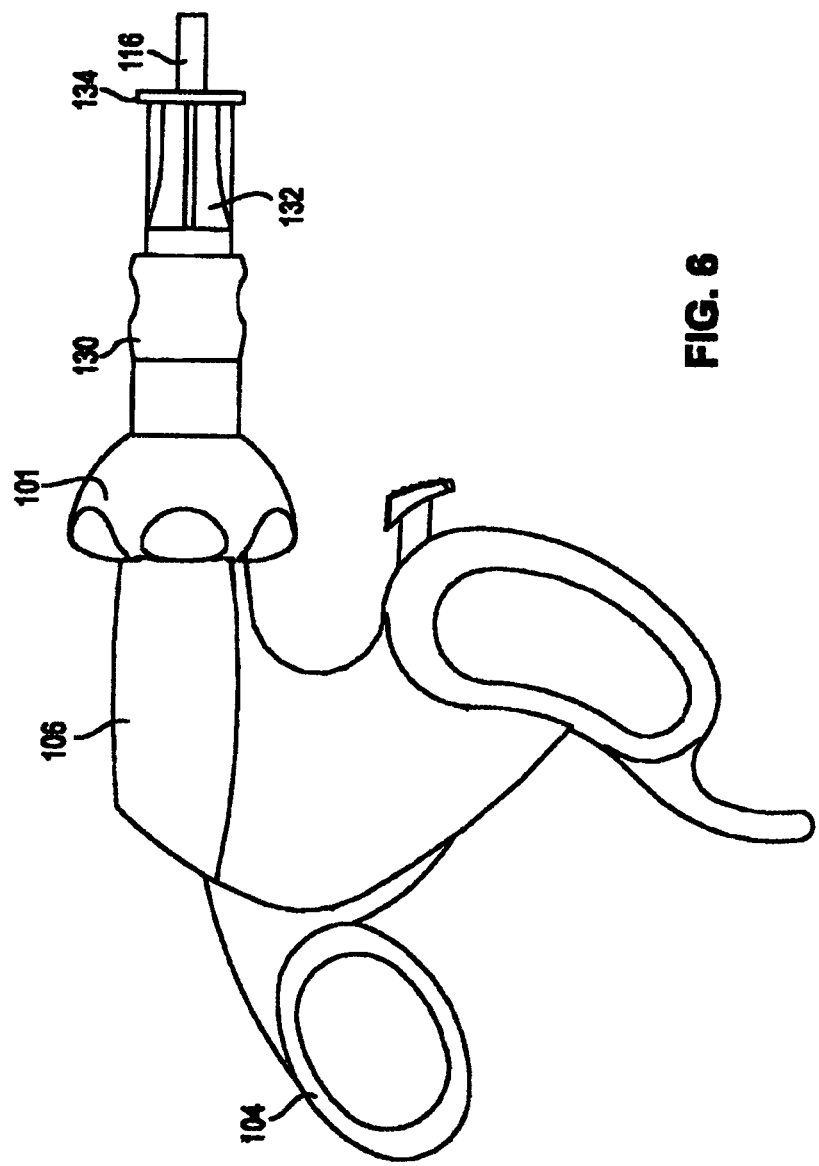
FIG. 6 is a side view of the proximal portion of a tool, showing the handle and proximal end of the shaft, with an articulation locking sleeve in a proximal and locked position.
Figure 7:
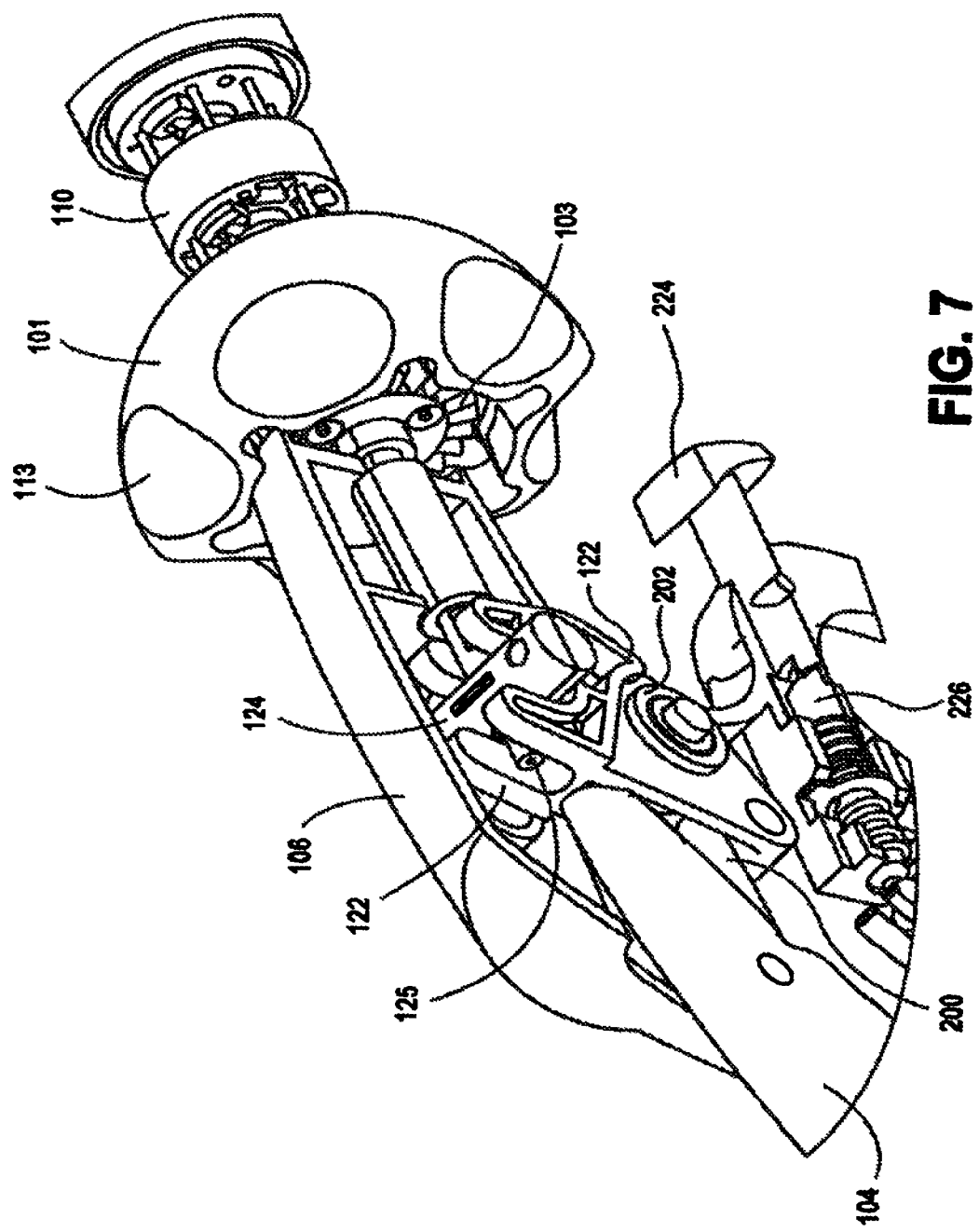
FIG. 7 is an exposed view of a portion of a tool from an overhead distal looking perspective, the portion including the handle, locking rotation knob, and a proximal link.

As shown in FIG. 6, a sleeve support mechanism 132 extends proximally from shaft 116 to provide sliding support for sleeve 130. A distal stop 134 provides a limit of distal movement of sleeve 130; a similar stop (not shown) is provided on or within handle 106 to limit proximal movement of sleeve 130. Detents, ridges or other mechanisms may be provided to maintain the sleeve in its proximal or distal positions and to provide tactile feedback to the user regarding the position of the sleeve. Further detail on mechanisms that control permissibility of articulation in articulatable instruments is provided in the concurrently filed and hereby incorporated U.S. Patent Application entitled "Tool with articulation lock" of Hegeman, Danitz, Hinman, and Alvord.

The description now turns briefly to features of tools that include embodiments of an inventive force limiter, such features including rotatability of the distal end effector by proximal mechanisms, and mechanisms by which rotatability is allowed or disallowed by a locking mechanism. Provided here will be a brief description of some these embodiments; a full disclosure of such embodiments is provided in concurrently filed and hereby incorporated U.S. Patent Application entitled "Tool with rotation lock" by Hinman and Danitz.

Figure 8:
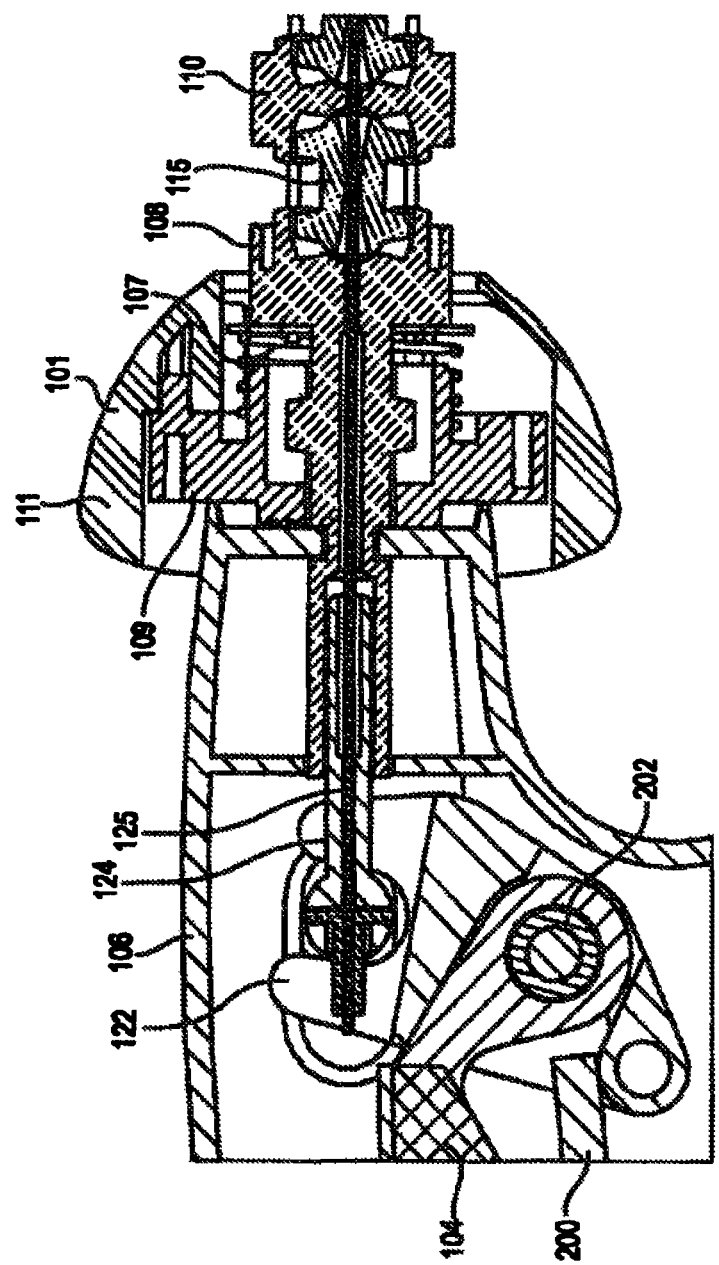
FIG. 8 is a cutaway view of a portion of the handle, knob, and a proximal link.
Figure 10:
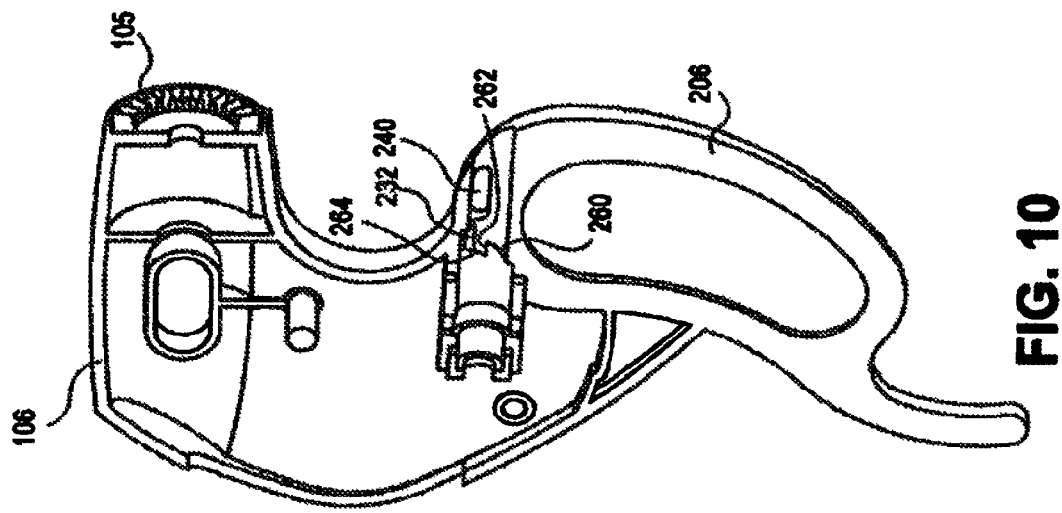
FIG. 10 is an exposed view of a handle from a proximal-looking perspective.
Figure 9:
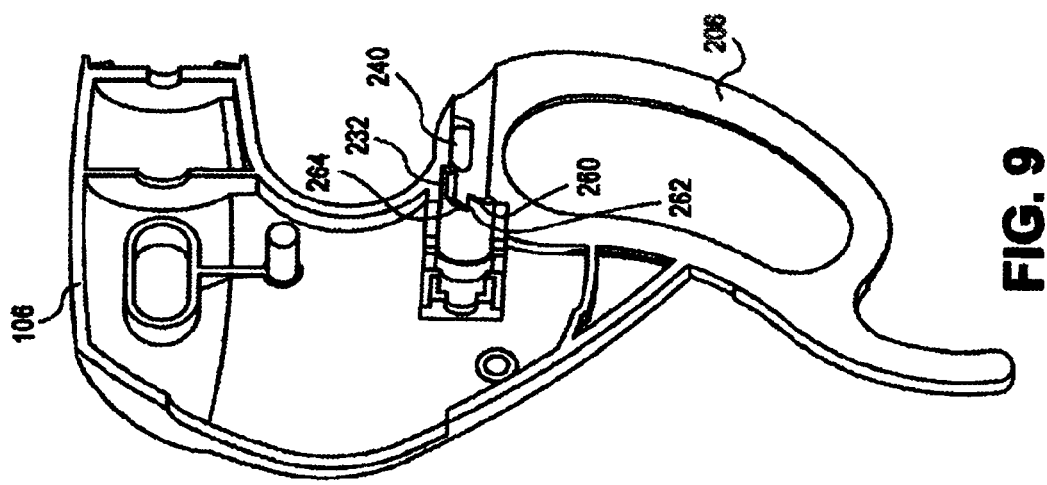
FIG. 9 is an exposed view of a handle from a distal-looking perspective.

The end effector 102 of tool 100 may be rotated with respect to handle 106 and then locked so that further rotation between end effector 102 and handle 106 is prevented. A rotation knob 101 is disposed at least partially around link 108. In the locked position, teeth 103 formed on the proximal face of knob 101 engage corresponding teeth 105 formed on a distal face of handle 106, as seen in FIG. 10. Handle 106 may be made in two pieces; two views of one of the two pieces are shown in FIGS. 9 and 10.) In this embodiment, the rotation lock is self-locking due to the action of a spring 107 biasing knob 101 proximally into engagement with handle 106, as shown in FIG. 8.

When moved distally against the bias of spring 107, the teeth 103 of knob 101 disengage from the teeth 105 of handle 106. This disengagement permits knob 101, links 108 and 110, shaft 106, links 112 and 114, and end effector 102 to rotate with respect to handle 106. This action permits the end effector to be rotated in any articulated configuration. When the end effector has been rotated the desired amount, release of knob 101 permits the two sets of teeth to re-engage, thereby locking the device against further rotation. In one embodiment, knob 101 is made in two pieces, an inner member 109 and an outer member 111, as shown in FIG. 8. The teeth 103 are formed on the inner member 109. Indentations or knurls 113 (FIG. 7) may be formed on knob 101 to facilitate grasping.

Description now turns to consideration of a force limiter that intervenes in the transmission of force from a user to an end effector on a tool. In the embodiments illustrated in FIGS. 1-20, the end effector 102 is a pair of jaws. Other end effectors (surgical, diagnostic, non-medical mechanical manipulators, etc) and end effector actuators may be used with the articulating tool of this invention. Actuation force is transmitted from movable end effector actuator 104 through a transmission or linkage that includes a rotatable rod actuator 122, a movable rod terminator 124, and a tension bearing member, such as rod 125 connected to rod terminator 124, as shown in FIGS. 3, 4, 7, and 8. Rod 125 passes through link 108, bushing 115, link 110; the shaft (not shown in FIG. 8) and the distal links (not shown in FIG. 8) to reach and actuate the end effector. Rod terminator 124 encases a portion of rod 125 within handle 106 to prevent the rod 125 from buckling under a compressive load. Similar features may be provided throughout the tool 100 to laterally constrain rod 125. (See further detail in concurrently filed patent application "Articulating tool with improved tension member system" of Hegeman, Danitz, Bertsch, and Alvord). End effector actuator 104 and rod actuator 122 are both rotatably mounted on a common bushing 202 so as to be able to be rotated with respect to each other to move rod 125 and thereby actuate end effector 102.

Figure 11:
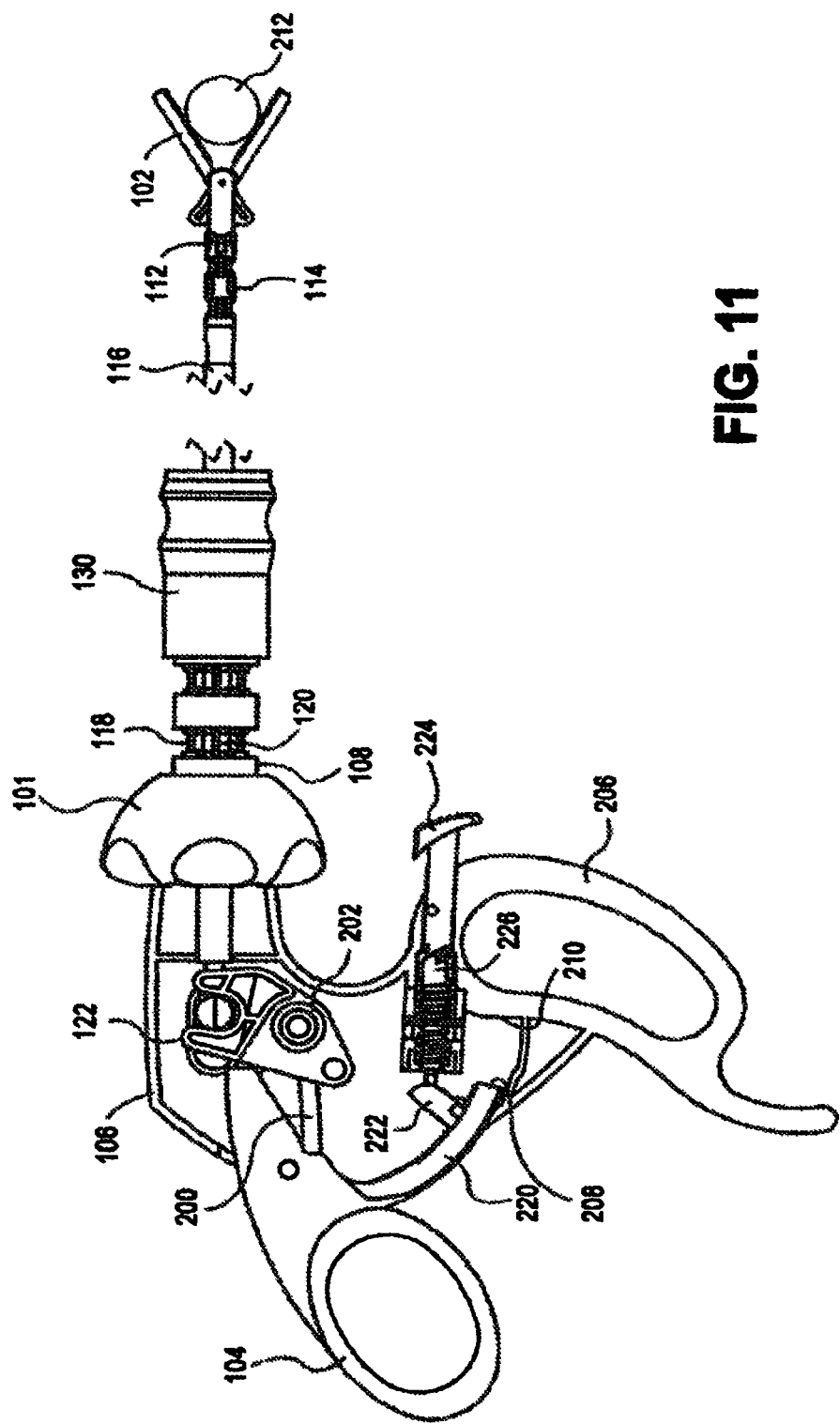
FIG. 11 is an exposed side view of a surgical tool with an end effector actuator and an end effector both in an open position, the end effector jaws embracing an object.
Figure 12:
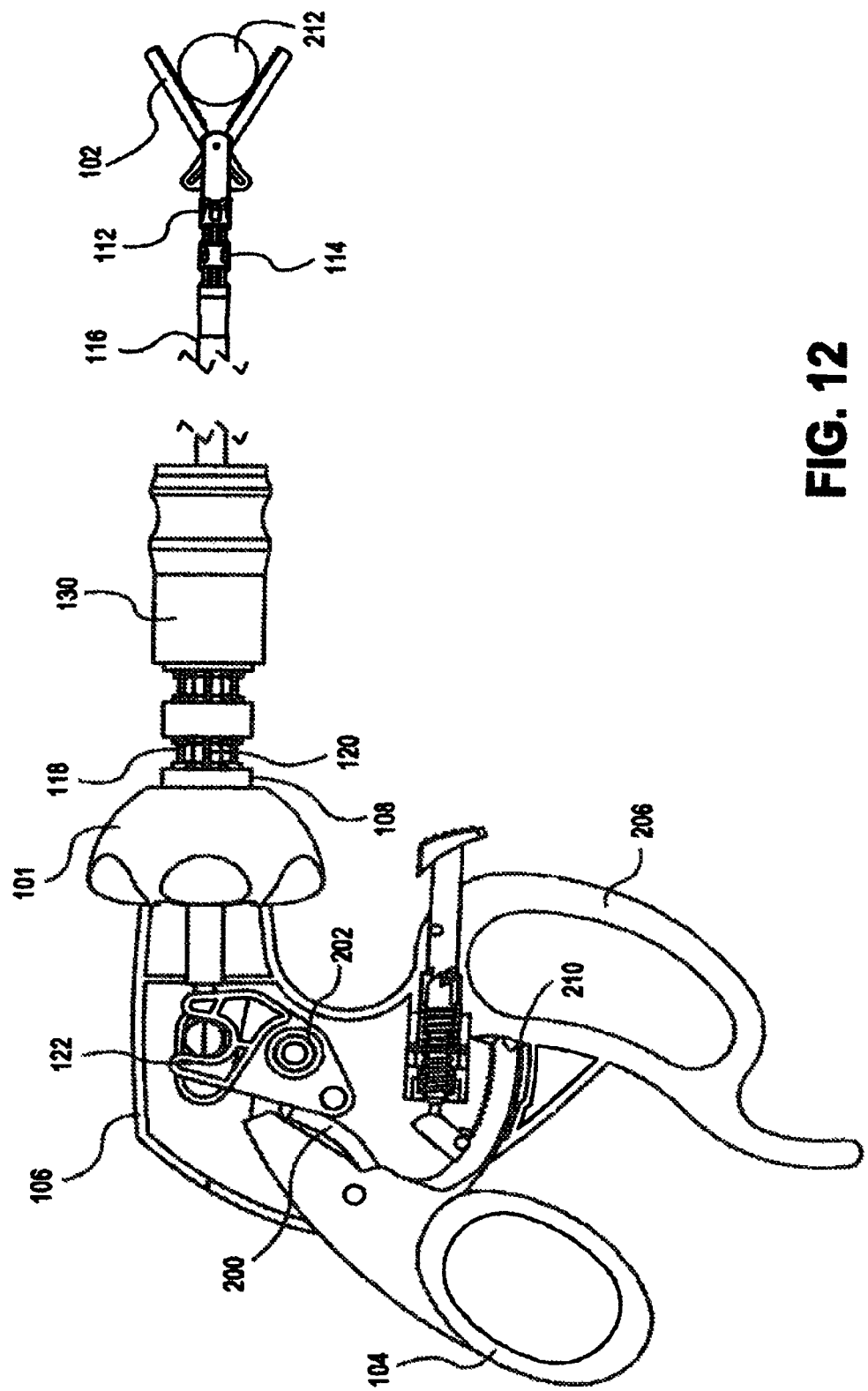
FIG. 12 is an exposed side view of a surgical tool with an end effector actuator in a closed position and the end effector in an open position, the end effect or jaws embracing an object, the force applied by the closed end effector actuator having been absorbed by a force limiter.
Figure 16:
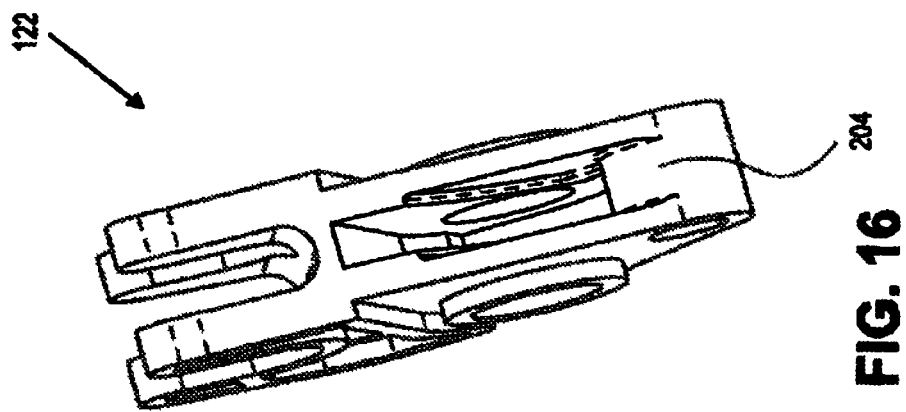
FIG. 16 is a side perspective, more sharply distal-looking view of a rotatable rod actuator, a ledge that engages the force limiter at the bottom.
Figure 15:
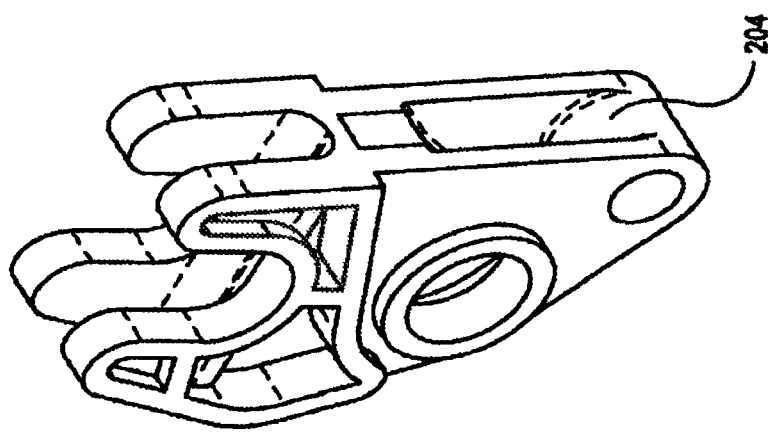
FIG. 15 is a side perspective, slightly distal-looking view of a rotatable rod actuator, a ledge that engages the force limiter at the bottom.

A force limiter such as a leaf spring 200 attached to end effector actuator 104 extends to a ledge 204 (shown best in FIGS. 15 and 16) formed in rod actuator 122 and provides for force transmission from the end effector actuator 104 to rod actuator 122 as actuator 104 is moved toward handle grip 206. Actuator 104 may be moved until a stop element 208 on a surface of actuator 104 engages a stop element 210 on grip 206, as shown in FIGS. 3 and 4 and in FIGS. 11 and 12. In FIG. 4, the end effector jaws are closed when actuator 104 engages stop element 210. In FIG. 12, on the other hand, the jaws have encountered an object 212. The force limiter of this invention permits the actuator 104 to continue moving toward stop element 210 even if the jaws have stopped closing while limiting the amount of force applied by the end effector on the object, as explained below.

Spring or force limiter 200 rotationally biases the rod actuator 122 against the end effector actuator 104 such that surface 250 of rod actuator 122 contacts surface 252 of end effector actuator 104 as shown in FIG. 13. In this embodiment, force limiter 200 is formed from a shape memory material (such as Nitinol) that is in its superelastic state. Force limiter 200 is pre-biased (to, e.g., 1.5% strain) so that it is at a known state along its stress/strain curve. This pre-loading of spring 200 ensures that, until a predetermined threshold force is reached (as described below), end effector 104, spring 200, bushing 202, and rod actuator 122 all move together and act as a rigid body. If the jaws of end effector 102 encounter an obstacle (as shown in FIG. 12) and the force applied through actuator 104 exceeds the threshold force, the stress on force limiter 200 reaches the characteristic plateau of the stress/strain curve, and force limiter 200 bends elastically substantially without delivering any further rotational movement to rod actuator 122, as shown in FIG. 14.

In one embodiment, the instrument has a force limiter 200 that establishes an upper limit on the actuation force that may be delivered to the end effector by the end effector actuator. In one embodiment, spring 200 may be formed from an elastomeric or spring metal material. In other embodiments, the material used to form spring 200 is selected and/or treated to provide a stress-strain relationship with a characteristic plateau region in which stress does not substantially change over a range of strain values. For example, in the instrument shown in FIGS. 1-19, spring 200 is formed from a superelastic shape memory material, such as Nitinol. The Nitinol is selected and treated so that spring 200 is in the Austenitic phase at the temperatures at which the instrument will be used. The material properties when so treated provide for substantially no change in stress over a range of strain values, e.g., 1.5% to 6% strain.

When assembling the instrument, spring 200 may be pre-loaded so that its strain is at or near the beginning of the stress plateau. In the absence of any counterforce resisting closing of the jaws of end effector 102, movement of end effector actuator 104 toward handle grip 206 transmits an actuation force through spring 200 to rod actuator 122, rod terminator 124, rod 125, and finally to end effector 102. As shown in FIGS. 11 and 12, if the jaws of end effector 102 encounter an object 212, actuator 104 will experience a counterforce as it continues its movement toward grip 206. When the counterforce exceeds the characteristic plateau stress of spring 200, spring 200 will deform without substantially increasing the strain of spring 200, thereby maintaining the actuation force transmitted through spring 200 and the remaining components of the actuation linkage. In the illustrated embodiment, the material comprising spring 200 may be selected and/or treated so that the spring remains in the stress plateau throughout its range of motion up to and including the point at which end effector actuator meets the limit stop 210 on grip 206.

Description now turns briefly to an actuator movement controller that may be included in embodiments of the invention depicted in FIGS. 1-20. Embodiments may include a shaft having a proximal end and a distal end, an end effector at the distal end of the shaft, a movable end effector actuator at the proximal end of the shaft and operably connected to the end effector, and an actuator movement controller operably connectable to the end effector actuator. The actuator movement controller includes a user-activated state changer that is changeable among several states. These states include ones in which the movement controller is (1) enabled and engaged with the end effector actuator to prevent movement of the end effector actuator in at least one of two opposing directions, (2) enabled and disengaged from the end effector actuator to permit movement of the end effector actuator in a first direction and a second direction opposite to the first direction in response to continuous user input via the state changer, and (3) disabled to permit movement of the end effector actuator in a first direction and a second direction opposite to the first direction in the absence of user input via the state changer. In some embodiments, the first state (enabled and engaged) may prevent movement of the end effector actuator in both directions.

In some embodiments the end effector includes jaws. In some embodiments the actuator movement controller includes a ratchet. In some embodiments the state changer includes a movable trigger. In some embodiments with a trigger, the state changer further includes a toggle operatively connected to the trigger so as to be movable with the trigger and to be rotatable with respect to the trigger. In some of the embodiments with a toggle, the toggle is operatively connected to the trigger so as to move with the trigger without rotating with respect to the trigger when the movement controller is enabled. Embodiments of the multi-state ratchet mechanism that controls the end effector and the end effector actuator are disclosed in detail in the U.S. Patent Application entitled and hereby incorporated "Tool with multi-state ratcheted end effector" by Hinman.

The embodiments described herein, by way of example, provide an actuator motion controller using a ratchet mechanism that, when engaged, permits the end effector actuator to be moved in one direction (to, e.g., close a pair of jaws) while preventing the end effector actuator to move in the other direction (to, e.g., maintain the jaws in their closed state). In FIG. 3, for example, the ratchet is formed from a rack of teeth 220 extending from end effector actuator 104. A movable pawl 222 is rotatably mounted within handle 106. A user may change the operation state of the ratchet by operating a trigger 224 which connects to pawl 222 through a toggle 226.

Figure 18:
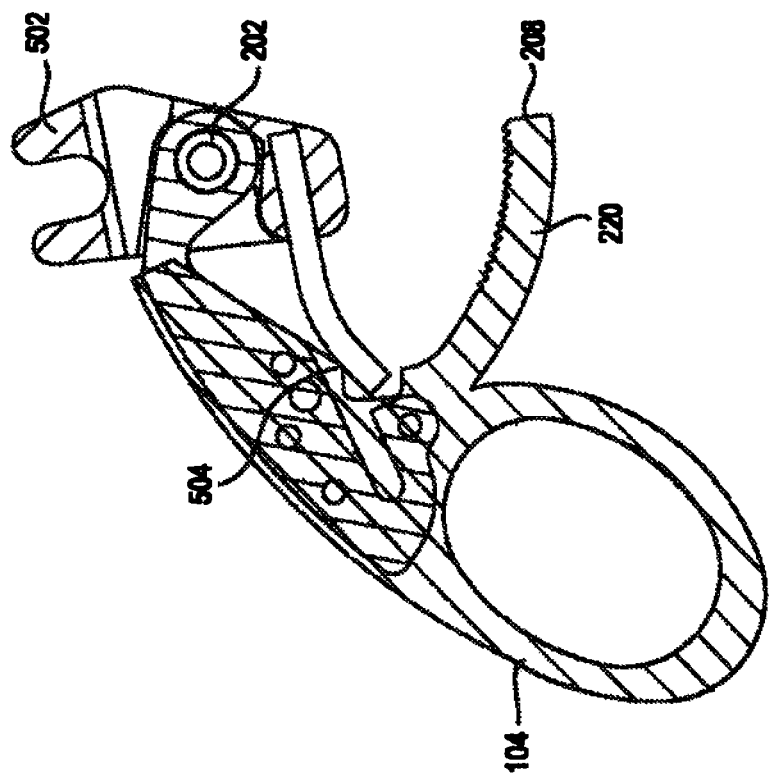
FIG. 18 is a cross sectional view of the force limiter locale of an instrument with the showing the end effector actuator in an closed position, and the force limiter having absorbed force from the closure of the end effector actuator, and thereby bent.

Returning now to the force limiter, FIGS. 17 and 18 show alternative embodiments of a force limiter according to this invention. Elements common to the embodiment shown in FIGS. 1-20 have been given the same reference numbers. As before, end effector actuator 104 and a rod actuator 502 independently rotate about a common bushing 202. This embodiment replaces the spring of the embodiment shown in corresponding FIGS. 3 and 4 with a spring 500 attached to rod actuator 502. Spring 500 engages end effector actuator at an engagement surface 504. As in the embodiment shown in FIGS. 1-16, spring 500 may be made from a superelastic shape memory material, such as Nitinol, and may be configured by design and/or assembly protocol such that it is preloaded to be at or near the plateau in its stress/strain curve. In that way, if a threshold actuation force is met, spring 500 deforms to the shape shown, e.g., in FIG. 18 without any additional stress being transmitted through the device's linkage to the end effector.

Figure 19:
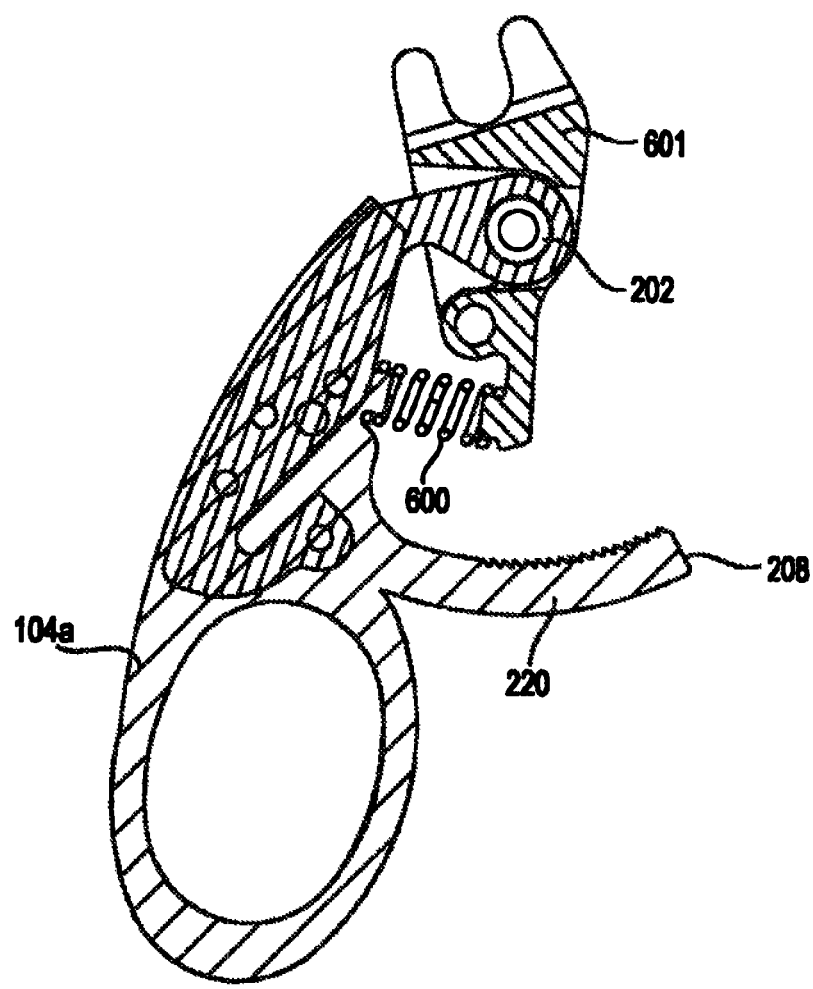
FIG. 19 is a view of the force limiter locale of an instrument, similar to the view provided in FIGS. 17 and 18, but with a different embodiment of a force limiter spring.

FIG. 19 shows yet another alternative embodiment of a force limiter according to the invention in a view that is similar to those of FIGS. 17 and 18. As before, an end effector actuator 104a and a rod actuator 602 independently rotate about a common bushing 202. In this embodiment, a coil spring 600 comprising a superelastic shape memory material such as Nitinol is pre-loaded and disposed between end effector actuator 104a and rod actuator 602. Pre-loading stress into the spring can place it at or near the plateau in its stress/strain curve, as described above. Consequently, as a threshold actuation force is applied, spring 602 deforms it without transmitting any additional stress through the device's linkage to the end effector.

Figure 20:
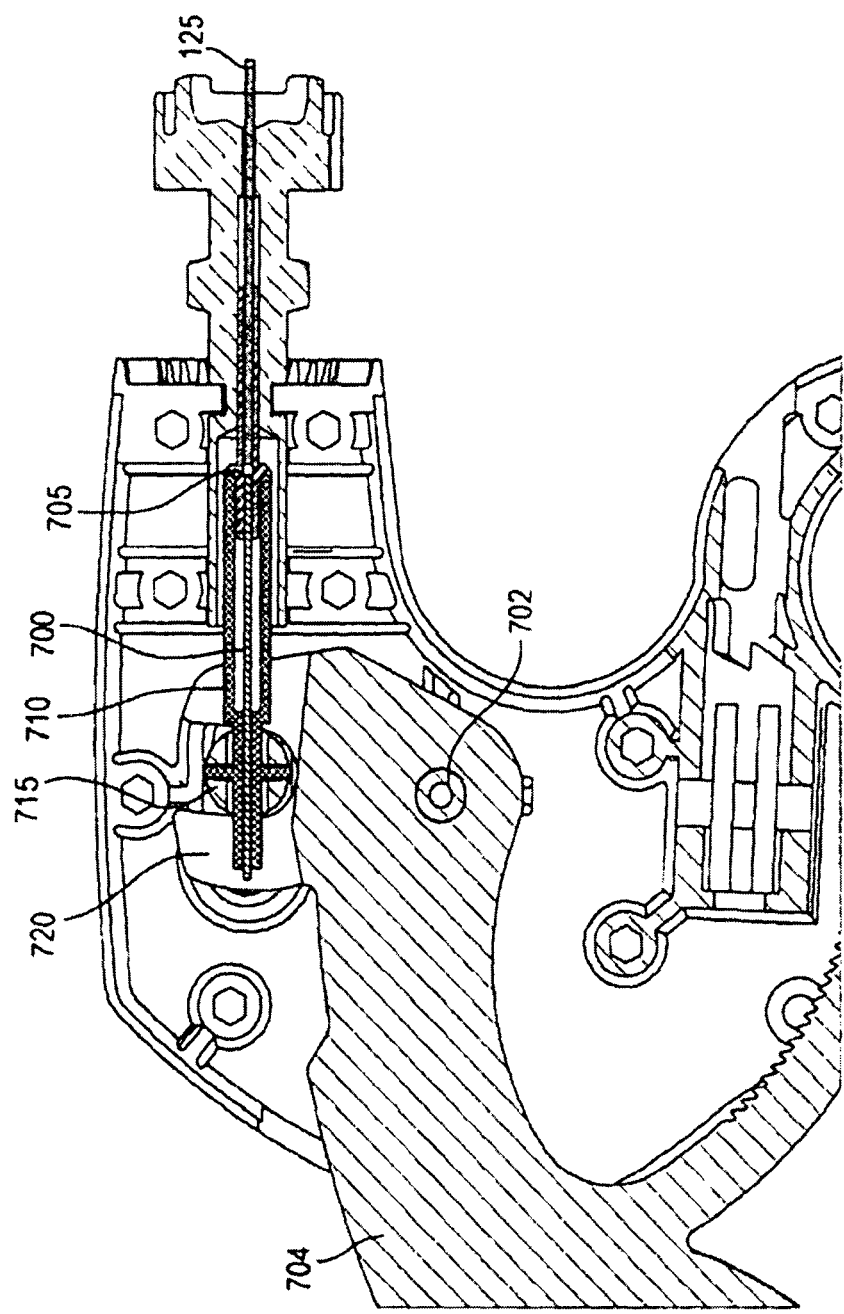
FIG. 20 is a cross sectional side view of a force limiter locale in a tool, wherein the force limiter is embodied as a linear actuator for an end effector actuating rod.

FIG. 20 shows still another embodiment of a force limiter. In this embodiment, the proximal end of end effector actuation rod 125 (optionally formed from Nitinol) is held in rod terminator 705. The distal end of a force limiter 700 is also held in rod terminator 705, while the proximal end of force limiter 700 is held in a force limiter housing 710. Rod terminator 705 fits into a distal opening of force limiter housing 710, but the two parts can be separated, as described below. In this embodiment, force limiter 700 is preloaded with a predetermined amount of stress at about or just below the plateau stress of a super elastic material, by, e.g., providing 1.5% strain in the position shown in FIG. 20. The distal portion of force limiter housing 710 is attached to a movable slide member 715, which fits in a fork 720 extending from end effector actuator 704. When end effector actuator 704 is rotated with a subthreshold force about bushing 702, fork 720 moves slide 715, force limiter housing 710, rod terminator 705 and rod 125 proximally to actuate the end effector. If the force applied to end effector actuator 704 exceeds the threshold force (due, e.g., to an object held in end effector jaws), force limiter 700 will stretch, separating force limiter housing 710 from rod terminator 705, so that further movement of end effector actuator 704 will not cause any further movement of rod 125. This feature limits the force delivered by the end effector actuator to the end effector, and consequently the force exerted by the end effector, to the threshold force.

In yet another embodiment (not shown) similar to that of FIG. 20, the rod 125 extends back into the linearly movable force limiter housing 710. By using Nitinol for rod 125, or another suitable super elastic material, if the force applied to rod 125 by end effector actuator 704 induces a stress equal to the plateau stress of rod 125, then rod 125 will stretch without increasing the force applied to the end effector.

While the inventive surgical instruments and devices have been described in some detail by way of illustration, such illustration is for purposes of clarity of understanding only. It will be readily apparent to those of ordinary skill in the art in light of the teachings herein that certain changes and modifications may be made thereto without departing from the spirit and scope of the appended claims For example, while the force limiter mechanism described herein typically has been in the context of a tool with an articulating mechanism comprising at least two links, the rotation knobs may be used in an instrument comprising only a single link, a multiplicity of links, with any number of cables or cable sets operably connecting the links, or, alternatively, embodiments of the inventive force limiter may be used with surgical instruments that do not articulate at all. Further, while the shaft of depicted instruments including embodiments of the force effector have been depicted as rigid, in some variations it may be desirable to have the handle affixed to a shaft that is flexible. Still further, while the inventive force limiter has been described in the context of a tool comprising a multi-state ratchet mechanism, some embodiments of the force limiter include tools without a ratchet mechanism. Lastly, while the context of the invention is typically understood to be surgical or medical diagnostic procedures, embodiments of the force limiter or tools having such a mechanism may have utility in other, non-medical contexts as well.

What is claimed is:

1. A medical tool comprising:
   an end effector at a distal end of the tool;
   an end effector actuator at a proximal end of the tool, the end effector actuator being operatively connected to the end effector through a linkage to deliver an actuation force from the end effector actuator to the end effector in response to movement of the end effector actuator, the linkage comprising an elongated actuation component defining an actuation axis;
   a rod terminator coupled to the elongated actuation component; and
   a force limitation assembly adapted to establish an upper limit on the actuation force delivered to the end effector by the end effector actuator, the force limitation assembly including an elongated force limiter component extending within and coupled to a force limiter housing, the force limitation assembly movably coupled to the end effector actuator and the force limiter housing removably coupled to the rod terminator,
       wherein when the actuation force delivered to the end effector actuator does not exceed the upper limit, the actuation force delivered to the end effector actuator causes linear movement of the elongated actuation component and the force limitation assembly along the actuation axis and
       wherein when the actuation force delivered to the end effector actuator exceeds the upper limit, the linear movement of the elongated actuation component is terminated.

2. The medical tool of claim 1 wherein when the actuation force exceeds the upper limit, movement of the end effector actuator causes at least a portion of the elongated actuation component to stretch.

3. The medical tool of claim 2 wherein the at least a portion of the elongated actuation component is formed from a shape memory material.

4. The medical tool of claim 1 wherein a portion of the elongated actuation component is held within the force limiter housing when the actuation force does not exceed the upper limit and separates from the force limiter housing when the actuation force exceeds the upper limit.

5. A medical tool comprising:
   an end effector at a distal end of the tool;
   an end effector actuator at a proximal end of the tool, the end effector actuator being operatively connected to the end effector through a linkage to deliver an actuation force from the end effector actuator to the end effector in response to movement of the end effector actuator, the linkage comprising an elongated actuation component defining an actuation axis; and
   a force limitation assembly adapted to establish an upper limit on the actuation force delivered to the end effector by the end effector actuator, the force limitation assembly movably coupled to the end effector actuator and removably coupled to the elongated actuation component,
       wherein when the actuation force delivered to the end effector actuator does not exceed the upper limit, the actuation force delivered to the end effector actuator causes linear movement of the elongated actuation component and the force limitation assembly along the actuation axis and
       wherein when the actuation force delivered to the end effector actuator exceeds the upper limit, the linear movement of the elongated actuation component is terminated,
       wherein the force limitation assembly includes an elongated force limiter component extending within a force limiter housing, and
       wherein the elongated actuation component comprises a rod terminator including a channel sized to receive a distal end of the force limiter component and including a coupling portion sized to extend within the force limiter housing.

6. The medical tool of claim 5 wherein when the actuation force delivered to the end effector actuator exceeds the upper limit, the coupling portion of the rod terminator separates from the force limiter housing.

7. The medical tool of claim 5 wherein the force limiter component is coupled to the rod terminator pre-loaded with a predetermined stress.

8. The medical tool of claim 1 wherein when the actuation force does not exceed the upper limit, the actuation force delivered to the end effector actuator causes sliding movement of the force limitation assembly along the actuation axis.

9. The medical tool of claim 1 wherein the actuation force on the end effector actuator causes rotational movement of the end effector actuator about a pivot.

10. The medical tool of claim 1 further comprising a movable slide member coupled to the force limitation assembly and slidable linearly along the actuation axis, wherein the end effector actuator includes a forked component that pivots with respect to the movable slide member when the actuation force is delivered to the end effector actuator.

11. The medical tool of claim 1 wherein the end effector comprises a pair of jaws.

12. The medical tool of claim 1, wherein the rod terminator includes a channel sized to receive a distal end of the force limiter component and includes a coupling portion sized to extend within the force limiter housing.

13. The medical tool of claim 12, wherein when the actuation force delivered to the end effector actuator exceeds the upper limit, the coupling portion of the rod terminator separates from the force limiter housing.

14. The medical tool of claim 1, wherein the force limiter component is coupled to the rod terminator pre-loaded with a predetermined stress.

15. The medical tool of claim 5, wherein when the actuation force does not exceed the upper limit, the actuation force delivered to the end effector actuator causes sliding movement of the force limitation assembly along the actuation axis.

16. The medical tool of claim 5, wherein the actuation force on the end effector actuator causes rotational movement of the end effector actuator about a pivot.

17. The medical tool of claim 5, further comprising a movable slide member coupled to the force limitation assembly and slidable linearly along the actuation axis, wherein the end effector actuator includes a forked component that pivots with respect to the movable slide member when the actuation force is delivered to the end effector actuator.

18. The medical tool of claim 5 wherein the end effector comprises a pair of jaws.

19. A medical tool comprising:
   an end effector at a distal end of the tool;

an end effector actuator at a proximal end of the tool, the end effector actuator being operatively connected to the end effector through a linkage to deliver an actuation force from the end effector actuator to the end effector in response to movement of the end effector actuator, the linkage comprising an elongated actuation component defining an actuation axis;

a force limitation assembly adapted to establish an upper limit on the actuation force delivered to the end effector by the end effector actuator, the force limitation assembly including an elongated force limiter component extending within and coupled to a force limiter housing, the force limitation assembly movably coupled to the end effector actuator and removably coupled to the rod terminator; and a rod terminator coupled to the elongated actuation component and including a channel sized to receive a distal end of the force limiter component, the rod terminator removably coupled to the force limiter housing, wherein when the actuation force delivered to the end effector actuator does not exceed the upper limit, the actuation force delivered to the end effector actuator causes linear movement of the elongated actuation component and the force limitation assembly along the actuation axis and wherein when the actuation force delivered to the end effector actuator exceeds the upper limit, the linear movement of the elongated actuation component is terminated.

20. The medical tool of claim 19, wherein when the actuation force delivered to the end effector actuator exceeds the upper limit, the rod terminator separates from the force limiter housing.

21. The medical tool of claim 19, wherein the force limiter component is coupled to the rod terminator pre-loaded with a predetermined stress.

22. The medical tool of claim 19, wherein when the actuation force does not exceed the upper limit, the actuation force delivered to the end effector actuator causes sliding movement of the force limitation assembly along the actuation axis.

23. The medical tool of claim 19, wherein the actuation force on the end effector actuator causes rotational movement of the end effector actuator about a pivot.

24. The medical tool of claim 19, further comprising a movable slide member coupled to the force limitation assembly and slidable linearly along the actuation axis, wherein the end effector actuator includes a forked component that pivots with respect to the movable slide member when the actuation force is delivered to the end effector actuator.

25. The medical tool of claim 19, wherein the end effector comprises a pair of jaws.

* * * * *